United States Patent [19]

Marino

[11] Patent Number: 4,733,654

[45] Date of Patent: Mar. 29, 1988

[54] INTRAMEDULLAR NAILING ASSEMBLY

[76] Inventor: James F. Marino, 2620 St. Tropez, La Jolla, Calif. 92037

[21] Appl. No.: 867,971

[22] Filed: May 29, 1986

[51] Int. Cl.[4] .............................................. A61F 5/04
[52] U.S. Cl. ........................ 128/92 YY; 128/92 YK; 128/92 YS; 128/92 YE
[58] Field of Search ....... 128/92 XX, 92 YK, 92 YV, 128/92 YT, 92 YS, 92 YZ, 92 YE, 92 VD, 92 YY

[56] References Cited

U.S. PATENT DOCUMENTS

| | | | |
|---|---|---|---|
| 3,002,514 | 10/1961 | Deyeerle | 128/92 YK |
| 3,107,666 | 10/1963 | Cerere et al. | 128/92 YK |
| 4,103,683 | 8/1978 | Neufeld | 128/92 YZ |
| 4,172,452 | 10/1979 | Forte et al. | 128/92 YK |
| 4,438,762 | 3/1984 | Kyle | 128/92 YV |
| 4,612,920 | 9/1986 | Lower | 128/92 YK |
| 4,622,959 | 11/1986 | Marcus | 128/92 YZ |
| 4,628,923 | 12/1986 | Medoff | 128/92 YK |

FOREIGN PATENT DOCUMENTS 1541151 12/1969 Fed. Rep. of Germany ........ 128/92 YK

OTHER PUBLICATIONS

"Intracapsular Fractures of the Hip", *Journal of Bone & Joint Surgery*, Myron O. Henry, 1934, p. 168.

Primary Examiner—C. Fred Rosenbaum
Assistant Examiner—H. Macey
Attorney, Agent, or Firm—Charmasson & Holz

[57] ABSTRACT

An intramedular nailing assembly, specifically adapted to the internal fixation of comminuted femoral fractures, which combines a conventional femoral nail, an extension and a set of pins interlocked with the nail and its extension. The extension is designed to be inserted into the proximal end of the femoral nail, and is pre-drilled to accept pins; some of which extend obliquely onto the femoral neck. A drill guide which can be inserted in the proximal end of the extension provides a convenient tool for pre-drilling the femur at the proper places and the proper angles. The nail itself can be pre-drilled to receive pins on a bench-mounted drilling guide.

10 Claims, 7 Drawing Figures

U.S. Patent   Mar. 29, 1988   Sheet 1 of 2   4,733,654
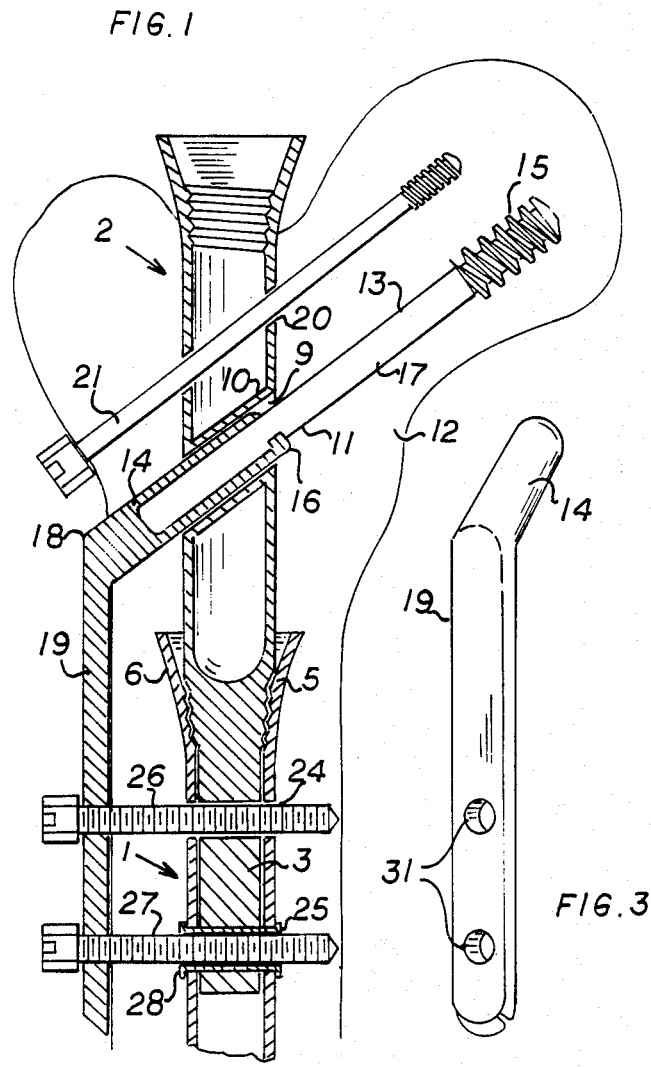
FIG. 1
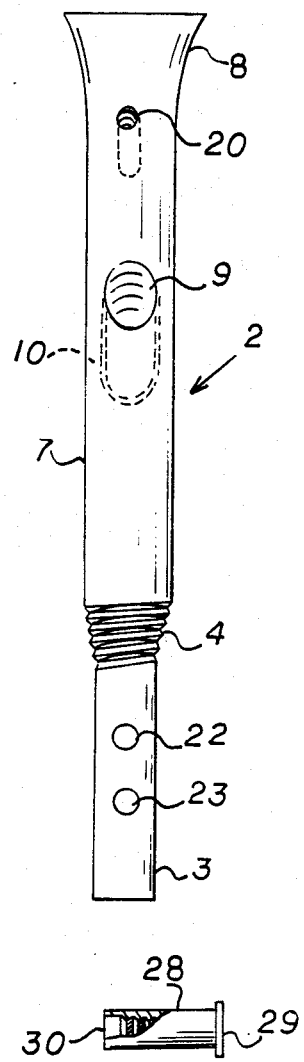
FIG. 2
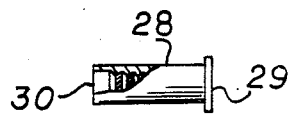
FIG. 4
FIG. 3

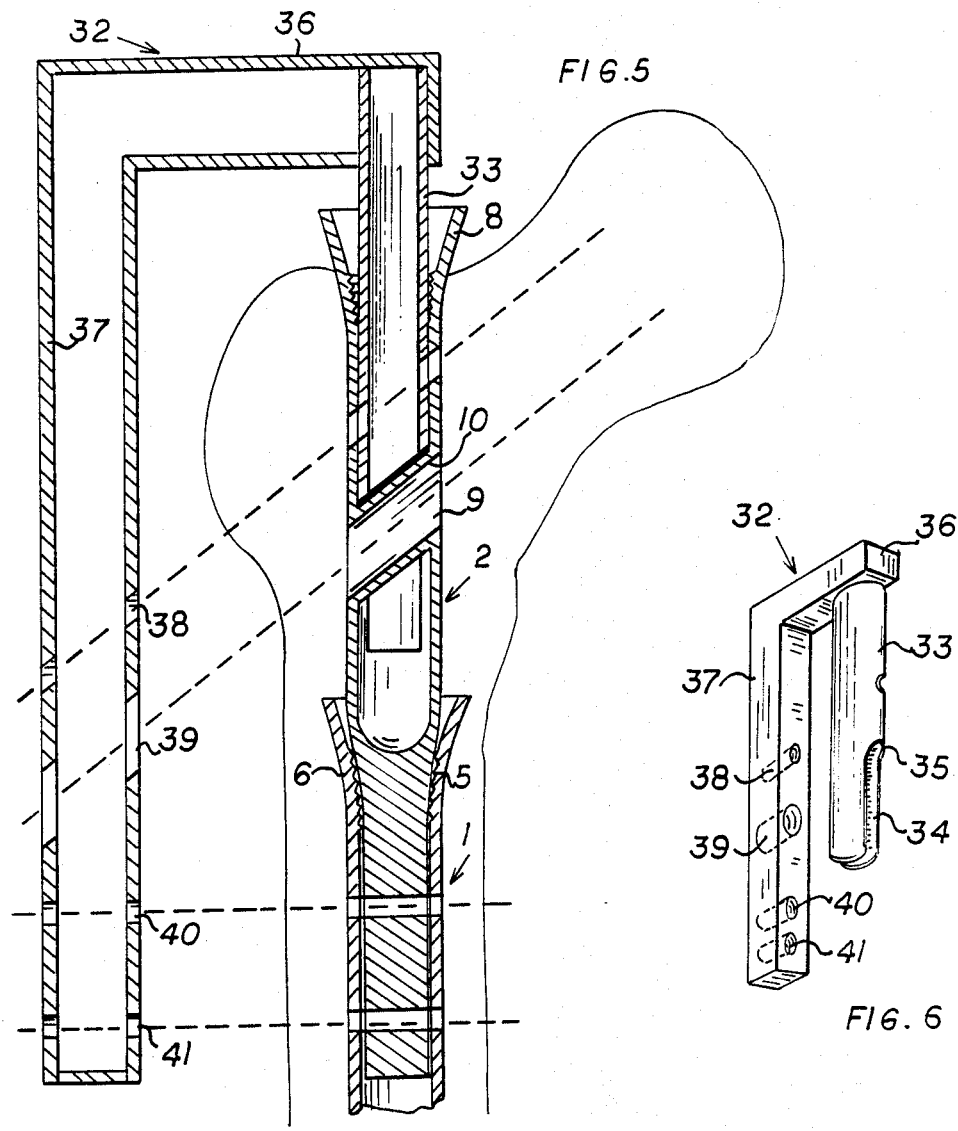

INTRAMEDULLAR NAILING ASSEMBLY

FIELD OF THE INVENTION

This invention relates to orthopedic bracing devices and more particularly to surgical fixation devices such as intramedullar splines, compression plates and pins which are installed temporarily to stabilize fractured bones during the healing process.

BACKGROUND OF THE INVENTION

Intramedullary nailing and alternate or ancillary fixation by means of plates and pins is a well established method of treatment for fractures of the femoral diaphysis.

This method is particularly indicated in case of severely comminuted, oblique and spiral fractures as well as fractures complicated by loss of bone, and fracture of the extreme proximal and distal ends of the femoral shaft.

However the now available intramedullar nail such as the so-called KUNTSCHER or SMITH-PETERSEN nail and other fluted nails, although extremely practical in the fixation of fractures affecting the middle third of the femur, presents severe limitations when used in the treatment of the extreme proximal end, fractures of the femoral neck and intracapsular fractures.

In a paper entitled "IPSILATERAL CONCOMITANT FRACTURES OF THE HIP AND FEMORAL SHAFT" published in the June 1979 issue of The Journal of Bone and Joint Surgery (Vol 61-A No. 4), the authors recommend that whenever a fracture of the femoral shaft is diagnosed roentgenograms of the hip should be made and carefully reviewed to detect undisplaced fractures of the neck and other occult intracapsular fractures. It is further recommended that all fractures be treated by internal fixation without traction.

That same paper discloses the use of so-called KNOWLES pins combined with the proximal end of the KUNTSCHER nail for fixing fractures of the femoral shaft. This approach requires the placement of pins or screws about the perimeter of the nail. Recently developed interlocking nail techniques (such as BROOKER-WILLS and GROSS-KEMPF) do not internally stabilize peritrochanteric and intracapsular fractures.

This would require the drilling of pin holes through the proximal end of the intramedullar nail. This procedure would assume that the surgical supply room of hospitals is well stocked in nails of various lengths and pre-drilled to accept orthogonally positioned pins for the fixation of the femoral shaft as well as obliquely oriented pins along the axis of the femoral neck. In reality most hospitals stock only a limited choice of nails with no pre-drilling. This limitation in available hardware imposes some fixation compromises upon the orthopedic surgeon at one of both sides of ipsilateral fractures and reliance on less effective techniques for treatment of femoral neck and intracapsular fractures.

SUMMARY OF THE INVENTION

The principal and secondary purposes of the invention are: to provide a universal kit for osteosynthesis and complex fracture fixation such as the fixation of comminuted femoral shaft fractures extending from the peritrochanteric region to the isthmus, including unstable comminuted fracture patterns of the proximal femoral diaphysis, in addition to fractures of the femoral neck and intracapsular fractures; to obviate the need for hospitals to stock multiple intramedullar nailing devices; to expand the scope of application of existing bone fixation appliances, and to limit the fixation compromises now imposed upon the othopedic surgeon in cases of combination fractures by the paucity and lack of versatility of current hardware.

These and other objectives are accomplished by means of a intramedullar fixation kit which combines a conventional femoral nail with an extension and a set of pins. A drill guide which can be inserted into the proximal end of the extension provides a convenient means for drilling the bone at the proper angle.

BRIEF DESCRIPTION OF THE DRAWING

FIG. 1 is a cross-sectional view of some of the elements of the kit applied to the fixation of a femoral neck fracture;

FIG. 2 is a front elevational view of the extension;

FIG. 3 is a perspective view of a side-plate;

FIG. 4 illustrates an immobilizing grommet;

FIG. 5 is a cross-sectional view of the bone drilling guide in position for actual use;

FIG. 6 is a reduced-scale, perspective view of the bone drilling guide; and

FIG. 7 is a perspective view of a bench nail drilling guide.

DESCRIPTION OF THE PREFERRED EMBODIMENT OF THE INVENTION

Referring now to the drawing there is shown in FIG. 1 the proximal end of a fractured femur which has been stabilized in accordance with the invention. An intramedullar fixation nail 1 such as the so-called Kuntscher nail or the like fitted with an extension 2 has been inserted axially through the medullar canal. The extension 2, also illustrated in FIG. 2, has a distal tip 3 with conical threads 4 dimensioned to match the female thread 5 in the proximal head 6 of the nail 1. The female thread 5 in the conical head of the nail is designed to receive the tip of an extracting tool (not shown on the drawing) which is commonly used to remove the nail after healing. The main body 7 of the extension is a hollow tube with a proximal head 8 similar to the proximal head 6 of the nail 1. Accordingly, the extracting tool can also be used to remove the nail and pin combination after healing of the bone. A first bore 9 surrounded by a tubular sleeve 10 is positioned transversally and obliquely on the median portion of the extension main body 7. As can be seen in FIG. 1, this bore receives a composite fixation pin 11 which extends into the femoral neck 12. The stem 13 of pin 11 in engaged into the barrel of a side-plate 19, and has a threaded tip 15 at the distal end. A key 16 at the mouth of the barrel cooperates with a groove 17 along the stem 13 to prevent axial rotation of the stem within the barrel 14. This type of barreled side-plate is well known in the art. Other versions of side-plate and pin combinations with other means of connection at the elbow 18 could alternately be used in the practice of the invention. A second but smaller and unsleeved bore 20 is drilled through the upper end of the extension at the same angle and parallelly to the first bore 9. The second bore 20 is designed to receive and direct a second smaller pin 21 as may be necessary to further stabilize the neck or intracapsular area against rotational movement. The distal tip 3 of the extension 2 is also drilled orthogonally to form two additional bores 22, 23 which are in line with symmetrical bores 24 and 25 in the proximal end of the nail 1. Threaded pins 26 and 27 engage said bores in order to stabilize the proximal end of the nail 1. For further stability the side plate 19 is captured at its lower end through bores 31 by pins 26 and 27.

It now can be understood that the just described fixation hardware offers the orthopedic surgeon a greater latitude in stabilizing not only combination fractures of the femoral diaphysis and peritrochanteric region, but also severely conminuted fractures of the proximal ends of the femoral shaft and intracapsular fractures.

FIGS. 5 and 6 illustrate a drilling guide 32 typically adapted for use with the just described intramedullar nail extension 2. The drilling guide 32 comprises a tubular positioning leg 33 shaped and dimensioned to engage into the proximal end 8 of the extension 2. It should be noted that the positioning leg 33 is not threaded but fits snugly into the extension 2. A bifurcated lower tip 34 engages the sleeve 10 with the upper end 35 of the forked tip 34 coming to rest against the upper edge of the sleeve 10. In that position any rotational movement of the guide 32 in relation to the extension 2 is prevented. A brace 36 is orthogonally connected to the upper tip of the positioning leg 33 and to a guide member 37 which extends distally but parallelly to the nail and extension assembly but outside the bone. The guide member 37 is drilled with a plurality of bores 38 through 41 which are in line with the various bores previously described in the proximal end of the nail 1 and of the extension 2. The positioning leg 33 is also drilled with bore 38 corresponding to the position of bore 20 in the extension and the second pin 21. The drilling guide 32 can thus be used by the surgeon once the nail and extension assembly have been installed to guide a drill bit through the bone and the various bores of the nail and extension. It should be noted that the alignment of bores 22 and 23 of the extension and bores 24 and 25 in the end of the nail can be verified before inserting the assembly through the medullar channel. It may be recommendable to immobilize the extension 2 within the nail in order to prevent rotation during insertions by installing a grommet 28 into lined up bores 23 and 25 as well as bores 22 and 24. The grommet 28 can be threaded on the inside to immobilize the nail and extension assembly by mechanical engagement of the side plate 19 and the nail 1. Alternatively, the inside of the grommet 28 could be left smooth in order to allow axial movement of the pin 27 therethrough. The choice of either type of grommet provides the surgeon with additional flexibility in the stabilization of calcar fractures depending whether or not compression is desired. FIG. 4 illustrates an internally threaded grommet 28 prior to installation with a flanged end 29. The opposite end 30 can be flared after insertion through the nail and extension and secured like a rivet.

FIG. 7 illustrates a bench type drilling guide 42 particularly adapted to pre-drill bores through the proximal and distal ends of the intramedullar nail. The first cavity 43 forms a channel opened at both ends to receive the proximal end of the nail 1. The flared end 44 is designed to receive the enlarged head 6 of the nail for exact positioning. Bores 45 and 46 intercepting the channel 43 are designed to guide the drill bit through the tubular nail. A second cavity 47 closed at one end 48 is designed to receive the distal end of the nail 1 for a similar purpose.

It should be understood that a variety of bench-type drilling guides could be devised according to the principle described here in order to accommodate various sections of the nail 1 or its extension 2. Similarly the drilling guide 32 could be extended, fixedly or by means of a telescopic arm to provide firm reference points when drilling in the median or distal part of the bone.

While the preferred embodiment of the invention has been described and some modifications have been suggested, other applications for the invention could be devised without departing from the spirit of the invention and the scope of the appended claims.

What is claimed is:

1. In combination with an intramedullary fixation nail designed for the fixation of femoral fractures, said nail having an axial head cavity shaped and dimensioned to receive an extracting tool, a modification kit which comprises:
   at least one pin; and
   a tubular nail extension having a distal end shaped and dimensioned to be axially inserted and secured into said axial head cavity, and at least one transversal bore dimensioned to engage said pin.

2. The combination claimed in claim 1, wherein said extension has a hollow core and a proximal end opening shaped and dimensioned to receive said extracting tool.

3. The combination claimed in claim 2, wherein said bore is directed obliquely to the axis of the nail extension and is surrounded by a sleeve.

4. The combination claimed in claim 3, wherein said kit further comprises:
   a drilling guide having a positioning leg shaped and dimensioned to be inserted into said proximal end opening, and having means for preventing axial rotation; and
   a guide member extending parallelly and distally from said extension, and having at least one hole sized and oriented to guide a drilling bit toward and through said bore when said positioning leg is inserted into the end opening of the extension.

5. The combination claimed in claim 4, wherein said means for preventing axial rotation comprises a bifurcated tip at the end of said positioning leg adapted to engage and rest against said sleeve.

6. The combination claimed in claim 3, wherein said kit further comprises a drilling guide block having at least one cavity shaped and dimensioned to snugly hold a section of said fixation nail and at least one transversal bore intercepting said cavity.

7. The combination claimed in claim 3, wherein the nail and the extension have respective transversal bores lined to allow the passage of a fixation pin therethrough.

8. The combination claimed in claim 7, wherein said kit further comprises at least one grommet dimensioned to pass through said transversal bores and be axially engaged by said fixation pin.

9. The combination claimed in claim 8, wherein said grommet and said fixation pin have engaging threads.

10. The combination claimed in claim 1 which further comprises a side-plate shaped and dimensioned to be mounted against a femoral head, said side-plate having a barrel projecting therefrom, said barrel being shaped and dimensioned to extend into said femoral head through said transversal hole and said barrel having an axial channel dimensioned to receive said pin and guide it into said femoral head.

* * * * *